(12) United States Patent
Kanjilal

(10) Patent No.: US 7,186,509 B2
(45) Date of Patent: Mar. 6, 2007

(54) DETECTION OF A GENETIC PREDISPOSITION TO CANCERS IN CATS

(75) Inventor: Sagarika Kanjilal, Shoreview, MN (US)

(73) Assignee: Andx, Inc., St. Paul, MN (US)

( * ) Notice: Subject to any disclaimer, the term of this patent is extended or adjusted under 35 U.S.C. 154(b) by 248 days.

(21) Appl. No.: 10/341,550

(22) Filed: Jan. 13, 2003

(65) Prior Publication Data

US 2003/0162212 A1    Aug. 28, 2003

Related U.S. Application Data

(60) Provisional application No. 60/347,757, filed on Jan. 11, 2002.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search ............ None
See application file for complete search history.

(56) References Cited

U.S. PATENT DOCUMENTS

2003/0092019 A1* 5/2003 Meyer et al. ............... 435/6

OTHER PUBLICATIONS

Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Mayr et al. (Br. Vet. J. vol. 151, pp. 325-329, 1995).*
Mayr et al. (Research in Veterinary Science, vol. 68, pp. 63-69 2000).*
Mayr, B. "Felis catus tumor suppressor p53 gene, intron 7" Genbank Accession No. U81298, Feb. 1997.*
Avigad, S., et al., "A novel germ line p53 mutation in intron 6 in diverse childhood malignancies", *Oncogene*, 14(13), (1997), 1541-1545.
Banerji, N., et al., "Alterations in Feline p53 in VAFS", *Genbank Database*, Genetic Sequence Listing, Accession No. AF175762, Felis catus p53 gene, intron 7,(Sep. 1999), 1 p.
Birch, J. M., et al., "Relative frequency and morphology of cancers in carriers of germline TP53 mutations," *Oncogene*, 20(34), (2001), 4621-4628.
Dewoody, J. A., "Nucleotide Variation in the p53 Tumor-Suppressor Gene of Voles from Chernobyl, Ukraine", *Mutation Research*, 439, (1999), 25-36.
Donehower, L. A., "The p53-deficient mouse: a model for basic and applied cancer studies", *Seminars in Cancer Biology*, 7(5), (1996), 269-278.
Evans, S. C., et al., "The Li-Fraumeni syndrome: an inherited susceptibility to cancer", *Molecular Medicine Today*, 3(9), (1997), 390-395.
Greenblatt, M. S., et al., "Mutations in the p53 tumor suppressor gene: clues to cancer etiology and molecular pathogenesis", *Cancer Research*, 54(18), (1994), 4855-4878.
Kanjilal, S., et al., "High frequency of p53 mutations in ultraviolet radiation-induced murine skin tumors: evidence for strand bias and tumor heterogeneity", *Cancer Research*, 53(13), (1993), 2961-2964.
Kanjilal, S., et al., "p53 mutations in nonmelanoma skin cancer of the head and neck: molecular evidence for field cancerization", *Cancer Research*, 55(16), (1995), 3604-3609.
Khaliq, S., et al., "P53 mutations, polymorphisms, and haplotypes in Pakistani ethnic groups and breast cancer patients", *Genetic Testing*, 4(1):, (2000), 23-29.
Kuperwasser, C., et al., "Development of spontaneous mammary tumors in BALB/c p53 heterozygous mice. A model for Li-Fraumeni syndrome.", *American Journal of Pathology*, 157(6), (2000), 2151-2159.
Malkin, D. et al., "Germ line p53 mutations in a familial syndrome of breast cancer, sarcomas, and other neoplasms", *Science*, 250(4985), (1990), 1233-1238.
Mayr, et al., "Novel p53 tumour suppressor mutations in cases of spindle cell sarcoma, pleomorphic sarcoma and fibrosarcoma in cats", *Veterinary Research Communications*, 22, (1998), 249-255.
Mayr, B., et al., "Polymorphisms in feline tumour suppressor gene p53, Mutations in an osteosarcoma and a mammary carcinoma", *Veterinary Journal*, 155(1), (1998), 103-106.
Menotti-Raymond, M., et al., "A genetic linkage map of microsatellites in the domestic cat (*Felis catus*)", *Genomics*, 57(1), (1999), 9-23.
Murphy, W. J., et al., "A radiation hybrid map of the cat genome: implications for comparative mapping", *Genome Research*, 10(5), (2000), 691-702.
Nambiar, et al., "Mutational Analysis of Tumor Suppressor Gene p53 in feline vaccine Site-Associated Sarcomas", *AJVR*, 61, (Oct. 2000), 1277-1281.
O'Brien, S. J., et al., "Comparative gene mapping in the domestic cat (*Felis catus*)", *Journal of Heredity*, 88(5), (1997), 408-414.
O'Brien, S. J., et al., "Comparative genomics: lessons from cats", *Trends in Genetics*, 13(10), (1999), 393-399.
O'Brien, S. J., et al., "The promise of comparative genomics in mammals", *Science*, 286, (1999),458-462, 479-481.
O'Byrne, K. J., et al., "Chronic immune activation and inflammation as the cause of malignancy", *British Journal of Cancer*, 85(4), (2001), 473-483.
Okuda, et al., "Cloning of feline p53 Tumor-Suppressor Gene and its Aberration in Hematopoietic Tumors", *Int. J. Cancer*, 58, (1994), 602-607.
Okuda, M., et al., "Molecular cloning and chromosomal mapping of feline p53 tumor suppressor gene", *Journal of Veterinary Medical Science*, 55(5), (1993), 801-805.
Srivastava, S., et al., "Germ-line transmission of a mutated p53 gene in a cancer-prone family with Li-Fraumeni syndrome", *Nature*, 348(6303), (1990), 747-749.

(Continued)

*Primary Examiner*—Jeanine A. Goldberg
(74) *Attorney, Agent, or Firm*—Brooks & Cameron, PLLC

(57) ABSTRACT

Methods are provided for the detection of susceptibility to cancer and non-cancerous pathologies in a mammal. Diagnostic kits are also provided.

7 Claims, No Drawings

OTHER PUBLICATIONS

Venkatachalam, S., et al., "Retention of wild-type p53 in tumors from p53 heterozygous mice: reduction of p53 dosage can promote cancer formation", *EMBO Journal*, 17(16), (1998), 4657-4667.

Verselis, S. J., et al., "Novel p53 splice site mutations in three families with Li-Fraumeni syndrome", *Oncogene*, 19(37), (2000), 4230-4235.

Yang, F., et al., "Reciprocal chromosome painting illuminates the history of genome evolution of the domestic cat, dog and human", *Chromosome Research*, 8(5), (2000), 393-404.

Nilanjana Banergi & Sagarika Kanjilil, Somatic Alterations of the p53 Tumor Supressor Gene in Vaccine-Associated Feline Sarcoma, AJVR, vol. 67, No. 10, Oct. 2006, pp. 1766-1772.

* cited by examiner

DETECTION OF A GENETIC PREDISPOSITION TO CANCERS IN CATS

CROSS-REFERENCE TO RELATED APPLICATIONS

This application claims priority to U.S. provisional patent application Ser. No. 60/347,757, filed on Jan. 11, 2002, which is incorporated by reference herein.

BACKGROUND OF THE INVENTION

Breeding practices over the years have inadvertently promoted and sustained a rather large number of genetic diseases, e.g., cancer and urinary system disorders, in cats and other animals (Vella et al., 1999). For example, several million domestic cats in the U.S. are predisposed to developing urinary system disorders, e.g., congenital urinary tract defects, polycystic kidney disease, neoplasia, renal failure, interstitial cystitis, urocystolithiasis, obstructions in the urethra or other parts of the urinary system, and urinary incontinence (Lekcharoensuk et al, 2001). Moreover, the ubiquitous mixed breed cat known as the domestic short hair and especially one of its parent breeds, the Siamese, have high cancer incidence rates with multiple malignancies occurring in relatively young cats (Vella et al., 1993; Hayes et al., 1981). The tumors seen in these breeds of cats are often sarcomas of soft tissues and bone. Before spaying of female kittens became a common practice, mammary tumors were the most common type of malignancy in cats (Ogilve and Moore, 1995).

Over the past decade, the incidence of sarcomas in cats has risen sharply with the mandatory administration of vaccines that commonly produce pronounced inflammatory reactions (Hendrick and Goldschmidt, 1991; Hendrick et al., 1992; Kass et al., 1993; Doddy et al., 1996; Banerji et al., 2001; Macy and Hendrick, 1996). While malignant transformation at injection sites has been documented in humans and other species, vaccine associated feline sarcoma (VAFS) has emerged as a serious problem in feline medicine with as many as ten-thirteen of every 10,000 vaccine injections leading to tumor formation (Macy and Hendrick, 1996; Marmelzat, 1968; Archampong and Clark, 1970). Since more than 53 million pet cats are administered one or more vaccines each year, a sizeable number of cats are at risk of developing the disease.

Diagnosing diseases in animals is not always an easy task. There are many examples of cases where the pets are treated repeatedly without resolution of the symptoms. In such cases, knowledge of a genetic predisposition to disease, e.g., cancer, VAFS, or a disorder of various organs such as the urinary system, endocrine system or cardiac disorder would indicate the possibility of disease development in the animal. Knowledge of disease predisposition in an animal would be extremely important in making treatment and management decisions. For example, certain treatment options may be less beneficial or even harmful to an animal predisposed to developing a disease such as cancer, VAFS, or a disorder of the urinary system. Regarding cancer, the availability and use of radiation therapy for treatment of cancers is increasing. This otherwise beneficial treatment may induce additional tumors in cancer-predisposed individuals. As for VAFS, cats that are predisposed to developing sarcomas at vaccination sites may benefit from special care and vaccination protocols during their lifetimes. Exposure to known physical, chemical or biological carcinogens could be eliminated or reduced and the individuals could be maintained on controlled diets. Routine visits to the veterinarian would include special attention to visible or palpable masses and other symptoms of possible disease development. Moreover, animals that are found to be predisposed to developing diseases or disorders of the urinary, cardiac, or endocrine systems are also likely to benefit from special care, diet, and medication during their lifetimes. In addition to preventive health maintenance, a simple genetic test would enable breeders to identify carriers and avoid mating animals that are susceptible to developing disease. Analysis of the incidence of a biomarker, e.g., a predisposing allele, in registered cats of various breeds would allow breeders to choose amongst cats without the disease-associated marker for perpetuating and improving the health of these breeds.

Thus, what is needed is a test for a molecular biomarker(s) that would allow pet owners and veterinarians to make informed decisions. What is needed is a test for detecting the predisposition of an individual to a disease such as cancer, e.g., VAFS, and/or the predisposition to a non-cancerous pathology including a disorder of the urinary, cardiac, and/or endocrine system. What is also needed is a diagnostic kit for such a test.

SUMMARY OF THE INVENTION

The inventor has discovered an association between a molecular biomarker with the predisposition to the development of various diseases and/or disorders in a mammal, such as a domestic cat. In one embodiment of the invention, the molecular biomarker is an, allele of feline p53 that is located on chromosome E1. There are known polymorphisms in intron 7 of feline p53, as indicated in the following sequence:

(SEQ ID NO:16)
5'-gtagggacccgca(c/t)gccaccctgccccaggccactctctcccgtgctaccgcccatcccgcctgtggaatcccg
cctgtggaatctcctctgctgtccccacccctccgcctccaagttttcttttctctggctttgggaccttctcttacccggc
ttctcgatactccttaggcttttaggctccacataggatgaaggaggtggggagtaagggggccccatctccctcactgcc
tccagcTTctgtcttctta(c/t)gtgggtag-3'.

The allele described herein contains an intronic alteration in intron 7 of p53, the alteration being a single thymidine (T) nucleotide insertion. To illustrate, the corresponding non-altered p53 allele sequence contains two Ts at nucleotide positions 246–247 of SEQ ID NO:16 (as indicated above by capitalization). The alteration-containing allele contains Ts at positions 246, 247 and 248 in intron 7 of p53, as indicated below:

5'-gtagggacccgcacgccaccctgccccaggccactctctcccgtgctaccgc
ccatcccgcctgtggaatcccgcctgtggaatctcctctgctgtccccaccc
tccgcctccaagttttcttttctctggctttgggaccttctcttacccggcttctcga
tactccttaggcttttaggctccacataggatgaaggaggtggggagtaaggg
gggccccatctcectcactgcctccagcTTTctgtcttcttacgtgggtag-3'
(SEQ ID NO:14, which is also GenBank Accession Number AF 175762).

Using the methods described herein, the susceptibility to a disease or disorder, i.e., the predisposition to the disease or disorder, can be detected in a mammal, e.g., a cat. In certain embodiments of the invention, the susceptibility to diseases such as cancer, for example, sarcomas of the soft tissues and bone (including fibrosarcoma, malignant fibrous histiocytoma, angiosarcoma, chondrosarcoma, liposarcoma, neurofibrosarcoma, schwannoma, lymphosarcoma, osteosarcoma), mast cell tumors, carcinomas (including squamous cell carcinoma, adenocarcinoma), melanoma, leukemias, myelomas, dedifferentiated tumor types and disseminated cancers, as well as tumors of specific organ systems (including endocrine organs such as the thyroid and adrenals, mammary glands, musculo-skeletal system, integumentary system, lymphatic system, etc.), and/or vaccine-associated feline sarcomas (VAFS) can be detected. In one embodiment, the cancer is a sarcoma or VAFS. In other embodiments of the invention, the susceptibility in a mammal to a non-cancerous pathology is detected. Non-cancerous pathologies include cardiac disease, disorders of the urinary system, and disorders of the endocrine system. "Cardiac disease" refers to any disease, disorder or condition of the cardiac system that is manifested by cardiac abnormalities or cardiac dysfunction, for example, that can lead to heart failure. For example, cardiac diseases include cardiomyopathy, hypertrophic cardiomyopathy, acute aortic regurgitation, tricuspid stenosis, constrictive pericarditis, acute infective endocarditis, ischemic heart disease, hypertension, primary myocardial disease, valvular disease, pericardial disease, arteriovenous fistula, Paget's disease, as well as heart murmur, valvular-associated murmur, valvular lesion and cardiac lesion. By "urinary system disorder" is meant, for example, congenital urinary tract defects, polycystic kidney disease, neoplasia, renal failure, interstitial cystitis, urocystolithiasis, obstructions in the urethra or other parts of the urinary system, and urinary incontinence. "Endocrine system disorder" refers to conditions of the adrenal gland or thyroid gland, such as nodules on the thyroid gland or hyperthyroidism.

In addition, methods and reagents for the detection and analysis of molecular biomarker, e.g., marker allele(s) of p53, which are associated with disease and/or disorder predisposition are described, and rapid methods for the detection of the predispositions have been developed and tested.

One embodiment of the invention provides detecting the susceptibility to cancer in a mammal, which method involves obtaining a biological sample from the mammal and detecting a molecular biomarker in the sample, wherein the molecular biomarker is a p53 allele with an alteration at position 246, 247 or 248 in SEQ ID NO:14 as compared to positions 246–247 in SEQ ID NO:16. The alteration can be a substitution, a deletion or an insertion, for example, an insertion of thymidine. The mammal can be, for example, a feline, such as a domestic cat. A "biological sample" refers to a sample of material that is to be tested for the presence of the molecular biomarker, e.g., a polynucleotide having the altered p53 allele described herein. The biological sample can be obtained from an organism, e.g., it can be a physiological sample, such as a blood sample, a tissue sample, or a mouth swab. Ordinarily, the biological sample will contain DNA including p53. The molecular biomarker can be detected by contacting the sample with a nucleic acid segment selected from SEQ ID NOs:1, 2, 3, 4, 5, 6, 7, 8, 9, 10, 11, 12, or 13. Once identified, the biomarker can be detected by methods generally known to the art, see, for example, Sambrook and Russell, *Molecular Cloning: A Laboratory Manual*, Cold Spring Harbor Laboratory Press Cold Spring Harbor, N.Y. (2001). By way of illustration, the biomarker can be detected by employing PCR, for example, allele-specific PCR, PCR-RFLP analysis, as well as by allele-specific hybridization, sequencing, etc.

Further provided is a method of detecting the susceptibility to a non-cancerous pathology in a mammal, involving obtaining a biological sample from the mammal and detecting a molecular biomarker in the sample, wherein the molecular biomarker is indicative of susceptibility in the mammal. For example, the molecular biomarker can be p53. The p53 can be detected by contacting the sample with a nucleic acid segment selected from SEQ ID NOs:1, 2, 3, 4, 5, 6, 7, 8, 9, 10, 11, 12, or 13. The alteration in the p53 can be one corresponding to positions 246, 247 or 248 of SEQ ID NO:14, as compared to positions 246–247 of SEQ ID NO:16. The alteration can be a substitution, a deletion or an insertion, such as an insertion of a thymidine. The non-cancerous pathology can be a urinary disorder; an endocrine system disorder, such as an adrenal gland disorder or a thyroid disorder, e.g., hyperthyroidism or thyroid gland nodules; or cardiac disease such as cardiomyopathy, heart valve dysfunction, heart murmur, valvular-associated murmur, cardiac lesion or a valvular lesion. In a particular embodiment, the mammal is a feline, such as a domestic cat.

The invention further provides a method of detecting the susceptibility to vaccine-associated feline sarcoma (VAFS) in a cat, which method involves obtaining a biological sample from the cat and detecting a molecular biomarker in the sample, wherein the molecular biomarker is indicative of VAFS susceptibility in the cat.

The invention further provides a method of detecting the susceptibility to cancer in a cat, which method involves obtaining a biological sample from the cat and detecting a molecular biomarker in the sample, wherein the molecular biomarker is a p53 allele comprising an alteration at positions 246, 247 and 248 of SEQ ID NO:14 as compared to position 246–247 of SEQ ID NO:16, wherein the molecular biomarker is indicative of cancer susceptibility in the cat.

Further provided is a method of detecting the susceptibility to a urinary disorder in a cat, which method involves obtaining sample from the cat and detecting a molecular biomarker in the sample, wherein the molecular biomarker is a p53 allele comprising an alteration at positions 246, 247 and 248 of SEQ ID NO:14 as compared to position 246–247 of SEQ ID NO:16, wherein the molecular biomarker is indicative of susceptibility to the disorder in the cat.

Further provided are diagnostic kits for detecting the susceptibility to cancer in a mammal; for detecting the susceptibility to a urinary disorder in a mammal; and for detecting the susceptibility to VAFS in a cat, which kits include packaging, containing a primer that specifically detects an alteration at position 246, 247 or 248 of SEQ ID NO:14 as compared to position 246–247 of SEQ ID NO:16. In one embodiment of the kit, the primer consists of SEQ ID Nos:1, 2, 3, 4, 5, 6, 7, 8, 9, 10, 11, 12 or 13. In addition to the primers described herein, the term "primer" refers to any primer that is capable of specifically detecting a molecular biomarker as described herein.

DETAILED DESCRIPTION OF THE INVENTION

The p53 gene product plays an important role in suppressing the formation of tumors. Somatic mutations (non-heritable DNA changes in a part of the body of the affected individual) of the gene have been extensively documented in various types of cancers (Greenblatt et al., 1994; Kanjilal et al., 1995; Kanjilal et al., 1993). Germ-line mutations (DNA alterations originating in sperm or ova that may be passed on to off-spring with the alterations then becoming present throughout the off-spring) in p53 are also present in about 60% of humans with the rare inherited cancer predisposition known as Li Fraumeni syndrome (LFS) (Srivastava et al., 1990; Malkin et al, 1990). Individuals with this disorder are prone to developing carcinomas of the breast and adrenal cortex as well as sarcomas of the bones and soft tissues (Evans and Lozano (1997); and Birch et al., 2001). Experimentally created transgenic mice lacking one or both functional alleles of p53 also develop sarcomas of the bones and soft tissues and provide a rodent model for studying the effects of germ-line mutations and tumor suppressor gene dosing (Donehower et al., 1996; Venkatachalam et al., 1998; Kuperwasser et al., 2000).

As companion animals, domestic cats are subjected to many of the same environmental conditions as their human co-dwellers. The feline genome displays the highest level of syntenic conservation with the human genome of all non-primates (e.g. cat pig, cattle, dog, mouse) that have been investigated (O'Brien et al. I; O'Brien et al., II; Menotti-Raymond et al., 1999, Murphy et al., 2000; Yang et al., 2000). The large number of genetic diseases with analogous pathologies described in the two species, as well as the high level of syntenic conservation between the feline and humans genomes, suggests that spontaneous diseases in domestic cats can provide useful models for investigating the etiology and molecular pathogenesis of many human diseases (O'Brien et al., 1999; Murphy et al., 2000; Chowdhary et al., 1998).

The possibility that the predisposition to cancer in domestic cats is similar to the inherited susceptibility to cancer observed in Li Fraumeni syndrome (LFS) prompted an investigation into the occurrence of germline alterations in the feline p53.

In addition to helping improve feline health management and treatment, the vaccine-associated sarcomas and genetic predispositions to disease susceptibility described herein is important in defining the role of inflammation in malignant transformation. Inflammation is believed to play an important role in the development of various types of cancer. (O'Byrne and Dalgleish, 2001). The clear connection between vaccine site inflammation and cancer development, as well as the ability to identify cats carrying the molecular bio-marker described herein, helps elucidate the cellular and molecular pathways of tumor development in response to inflammation and the identification of targets for preventing or slowing the process.

Predisposed cats develop cancers, such as sarcomas, that also afflict humans. The success rate for treatment of cancers such as sarcomas needs to be improved for both pet animals and humans. The predisposed cats that develop cancer provide natural models for basic research as well as for the evaluation of chemotherapeutics and other treatments with potential anti-cancer activities. Cell lines developed from the feline cancers provide valuable materials for conducting ex vivo research while the feline cancer patients provide test subjects for in vivo evaluation of treatment protocols. Hence, a feline model for human—cancer predisposition and cancer treatment is also envisioned in this disclosure.

The invention will now be illustrated by the following non-limiting Examples.

EXAMPLE 1

Methods:

Study cases and controls. Biological samples including blood and tissue samples were obtained from 33 VAFS cases and matched cancer free controls. The cases included 20 male domestic short hairs (DSH), 13 female DSHs, and their average age was 8.5 (range 1.5–16). Cases were matched with controls by age (+/−1 year) and sex.

PCR Amplification and sequence analysis of feline p53. Segments of feline genomic DNA spanning exons 5 through 9 of the p53 gene were amplified using oligonucleotide primers as shown in Table 1 (Saiki et al., 1988).

TABLE 1

| Segments | Primers | | Size (bp) |
|---|---|---|---|
| Exon 5 + intron 5 + Exon 6 | 5'-tactccctcccctcaacaa-3'<br>5'-cagacctcgggcggctc-3' | (SEQ ID NO:1)<br>(SEQ ID NO:2) | 386 |
| Exon 7 + intron 7 + Exon 8 | 5'-gtcggctctgactgtacc-3'-<br>5'cttacctcgcttagtgctcc-3' | (SEQ ID NO:3)<br>(SEQ ID NO:4) | 519/520 |
| Intron 7 (partial) + Exon 8 +<br>Intron 8 + Exon 9 (partial) | 5'-ctttgggaccttctcttacc-3'<br>5'-attctccatccagtggcttc-3' | (SEQ ID NO:5)<br>(SEQ ID NO:6) | 330 |

Amplification reactions contained 50 ng genomic DNA template, 0.2 μM each of forward and reverse primers, 100 μM dNTPs, 0.75 U AmpliTaq Gold (Perkin Elmer, Foster City, Calif.), and PCR Buffer I (Perkin Elmer) in a total volume of 25 μL. The AmpliTaq Gold in the reactions was activated at 94° C. for 10 minutes. Amplification using the first two primer pairs was performed using annealing temperatures of 65° C. for 2 cycles, 60° C. for 3 cycles, and 55° C. for 25 cycles. An annealing temperature of 55° C. was maintained for 30 cycles for amplification using the third primer pair. Extension and denaturation temperatures were maintained at 72° C. and 94° C., respectively, and all segments of each amplification cycle were 30 seconds in duration (except on the last cycle for which the extension period was increased to 5 min).

Examples of additional primers useful for the detection and examination of segments of feline p53 include:

| | |
|---|---|
| 5'-ccg ccg ttg gaa ctc ac-3' | (SEQ ID NO:7) |
| 5'-agt aac cga ctt ggc tg-3' | (SEQ ID NO:8) |
| 5'-ggt ttc cat tta ggg ttc-3' | (SEQ ID NO:9) |
| 5'-gca cgg ggc agg tct tcg-3' | (SEQ ID NO:10) |

The molecular biomarker described herein can also was detected by examination of the nucleic acid segment amplified by the primer 5'-cca gca tct cat ccg agt gg-3' (SEQ ID NO:11) and a suitable down-stream primer such as SEQ ID NO:4 or SEQ ID NO:6.

Nucleotide sequence analysis. Amplicons were filtered through Microcon-100 (Amicon Inc., Beverly, Mass.) and sequenced in both directions using AmplitaqFS Dye-terminator chemistry (PE Applied Biosystems, Foster City, Calif.). The sequencing reaction mixtures were electrophoresed on ABI model 377 DNA sequencers (PE Applied Biosystems) at the University of Minnesota Advanced Genetic Analysis Center. The sequence data was analyzed using EditSeq and MegAlign programs (DNA Star, Madison, Wis.).

Statistical Methods. The distribution of the alleles in cancer cases and cancer-free controls was analyzed by Fisher's exact test (Statview 5.0, SAS Institute, Cary, N.J.). The confidence interval for the analyses was set at 95%.

Allele-Specific PCR Analysis. The predisposing allele was amplified and detected by PCR amplification using the allele specific primer 5'-ccc tca ctg cct cca gct tt-3' (SEQ ID NO:12) and a down-stream primer such as SEQ ID NO:4 or SEQ ID NO:6. The allele not associated with the disease predisposition was amplified and detected by PCR amplification using the primer 5'-ccc tca ctg cct cca gct tc-3' (SEQ ID NO:13) and a down-stream primer such as SEQ ID NO:4 or SEQ ID NO:6. The conditions for PCR (e.g. temperature and time) were adjusted as needed. For example, an annealing temperature of 55° C. for 30 cycles of amplification was suitable for amplification with the primer pair SEQ ID NO:12 and SEQ ID NO:6 and the primer pair SEQ ID NO:13 and SEQ ID NO:6.

PCR-Restriction Fragment Length Polymorphism (RFLP) Analysis. Detection of the allele containing the molecular biomarker was accomplished by the use of RFLP analysis, a method which is known to the art. For example, the PCR product obtained on amplification with primers SEQ ID NO:3 and SEQ ID NO:4 was cut and analyzed with the restriction enzyme AlwNI, SpHI, or BsaAI.

Allele specific hybridization. Analysis of the molecular biomarker was conducted by hybridization of labeled nucleic acid probes. The oligonucleotides SEQ ID NO:12 and SEQ ID NO:13 are examples of probes that were used for this purpose. Hybridization techniques are known to the art.

Results

The genomic sequence of feline p53 was examined from exons 5 through 9 in blood or normal tissue samples obtained from 33 domestic short hair cats with vaccine associated feline sarcoma and an equal number of age, sex, and breed matched cancer-free controls. Seven sites of allelic variation have been found to date. Three previously identified polymorphic sites were found in exon 5 and intron 7 (Okuda et al., 1993; Mayr et al., 1998). Four additional sites of allelic variation have been found. One of these newly recognized sites involved a single thymidine (T) nucleotide insertion in intron 7 as, shown by the sequence 5'-gtaggga cccgcacgccaccctgocccaggccactctctcccgtgctaccgocccatcccg cctgtggaatcccgcctgtggaatctcctctgctgtcccacccctccgcctccaag ttttcttttctctggctttgggaccttctcttacccggcttctcgatactccttaggcttta ggctccaca taggatgaaggaggtggggagtaagggggggcccccatctccctcac tgcctccagc<u>TTT</u>ctgtcttcttacgtgggta g-3' (SEQ ID:14; with altered area capitalized and underlined, also noted in Genbank Accession number AF175762), while the other three sites involved single nucleotide polymorphisms in intron 8 (5'-gta agc ggg cag ga(c/t) gag a(g/a)g agg cag gga ggg tgc agt tcg gct caa aat tta ctc ttc tct cgc cgt (t/c)cc tca cct ctt tcc cag (SEQ ID NO:15) (with polymorphisms at positions 15, 20, and 70 indicated by nucleotides in parenthesis).

Analysis of the allelic distribution at the polymorphic sites in germline DNA from this series of cases and cancer-free controls indicated that the allele containing the single nucleotide insertion in intron 7 is specifically associated with the development of tumors (Table 2). This allele was present in 16 of the 33 (49%) VAFS cases that were examined. Fourteen cases were heterozygous (+/−) for the allele and another two were homozygous (+/+). In contrast, none of the 33 cancer-free controls were homozygous for the allele and only three (9%) harbored the allele in the heterozygous state. A two-tailed Fisher's test showed that the association between this allele and the development of cancer was significant (p<0.001). The odds ratio for this case-control study was >9.4.

TABLE 2

Distribution of the p53 allele containing an intron7 insertion in 33 VAFS cases and matched cancer-free controls

| Alleles | Cases | Controls |
|---------|-------|----------|
| +/+     | 2     | 0        |
| +/−     | 14    | 3        |
| −/−     | 17    | 30       |

Cases included 20 male and 13 female domestic short hair cats (DSH).
Controls were also DSH and matched to cases (1:1) by age and sex.

Discussion

Although the feline marker allele of p53 described herein bears an intronic alteration and many of the alterations found in human LFS commonly occur in exons 5–9, intronic alterations of p53 have also been described in families that fit the LFS description (Srivastava et al., 1990; Malkin et al., 1990; Evans and Lozano, 1997; Verselis et al., 2000; Avigad et al., 1997; Khaliq et al., 2000). Some of these intronic alterations lead to alternately spliced forms of p53 but in other cases the mechanism by which the intronic sequences are associated with the cancer predisposition are yet unknown (Verselis et al., 2000; Avigad et al., 1997; Khaliq et al., 2000).

The results described herein indicate that the single nucleotide insertion that is associated with cancer development in domestic short hair cats is also present in cancer cases amongst cats of the Siamese and its derivative breeds. The combination of the genetic predisposition and the founder effect in the domestic cat population has likely resulted in the marked rise in the incidence of sarcomas following enactment of laws mandating vaccinations in various states (Hendrick and Goldschmidt, 1991, Vella et al., 1999; Vinogradov, 1997; Klein et al., 1988).

EXAMPLE 2

Predisposition in Domestic Cats to Cancers

Analyses on 115 other cancers in the domestic cat, including various carcinomas, adenomas, lymphomas, sarcomas, mast cell tumors, leukemias, myelomas, and melanomas, representing tumors of various organs including breast, skin, muscle, nerve, bone, thyroid glands also indicated the presence of a genetic predisposition. Comparison of the presence of susceptibility markers in cases as compared to controls also indicated that the associations were highly significant for each cancer type (p values<0.05).

EXAMPLE 3

Predisposition in Domestic Cats to Non-Cancerous Pathologies

Review of the medical history for the control cats described in Example 1 revealed a clinical history of urinary system disorders in some individuals.

Blood samples from six cats with a history of urinary system disorder (case) and 19 control cats (no history of urinary disorder) were collected. PCR amplification of feline p53 and sequence analysis of amplicons was conducted as described in Example 1.

Results

TABLE 3

Data Indicating Predisposition to Urinary System Disorders

| Marker | Case | Control |
|---|---|---|
| Present | 4 | 1 |
| Absent | 2 | 18 |

Statview analysis indicated highly significant p-values:

| Summary Table for Rows, Columns | |
|---|---|
| Num. Missing | 0 |
| DF | 1 |
| Chi Square | 10.746 |
| Chi Square P-Value | .0010 |
| G-Squared | 9.547 |
| G-Squared P-Value | .0020 |
| Contingency Coef. | .548 |
| Phi | .656 |
| Cty. Cor. Chi Square | 7.377 |
| Cty. Cor. P-Value | .0066 |
| Fisher's Exact P-Value | .0055 |

As with the cancer, the single nucleotide insertion in intron 7 of p53 described herein is associated with urinary system disorders in cats. Four out of six of the urinary disorder cases were positive for the allele, whereas one out of 18 of the control animals were positive. Similarly, a number of cats with the marker allele also have a history of cardiac problems or endocrine disorders.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

REFERENCES

Archampong and Clark, *Br. J. Surg.*, 57, 937–938 (1970).
Avigad et al., *Oncogene* 14, 1541–1545 (1997).
Banerji et al., *Am. J. Vet. Res.* 63, 728–732 (2002).
Birch et al., *Oncogene* 20, 4621–4628, (2001).
Doddy et al., *J. Comp. Path.*, 114, 165–174 (1996).
Donehower, *Seminars in Cancer Biol.* 7, 269–278 (1996).
Evans and Lozano, *Mol. Med. Today*, 3, 390–395 (1997).
Greenblatt et al., *Cancer Res.* 54, 4855–4878 (1994).
Malkin et al., *Science* 250, 1233–8, (1990).
Hayes et al., *Vet. Record* 108, 476–479 (1981).
Hendrick and Goldschmidt, *J. Am. Vet. Med. Assoc.* 199, 968 (1991).
Hendrick et al., *Cancer Res.*, 52, 5391–5394 (1992).
Kanjilal et al., *Cancer Res.* 55, 3604–3609, 1995.
Kanjilal et al., *Cancer Res.* 53, 2961–2964 (1993).
Kass et al., *J. Am. Vet. Med. Assoc.*, 203, 396–405 (1993).
Khaliq et al., *Genetic Testing* 4, 23–29 (2000).
Klein et al., *J. Hered* 79, 389–393 (1988).
Kuperwasser et al., *Am. J. Path.* 157, 2151–2159 (2000).
Lekcharoensuk et al., *J. Am. Vet. Med. Assoc.*, 218, 1429–35 (2001).
Macy and Hendrick, *Vet. Clinics of North America*, 26, 103–109 (1996).
Marmelzat, *Arch. Dermatol.*, 97, 400–406 (1968).
Mayr, et al., *Vet. J.* 155, 103–106 (1998).
Menotti-Raymond et al., *Genomics*, 57, 9–23 (1999).
Murphy et al., *Genome Res.*, 10, 691–702 (2000).
O'Brien et al., *Science*, 286, 458–62, 479–81 (1999).
O'Brien et al., *J. Hered.*, 88, 408–414 (1997); O'Brien I.
O'Brien et al., *Trends Genet.*, 13, 393–399 (1997); O'Brien II.
Ogilve and Moore, In: Managing the Veterinary Cancer Patient, Veterinary Learning Systems, 1995.
O'Byrne and Dalgleish, *Br. J. Cancer*, 85, 473–83 (2001).
Okuda et al., *J. Vet. Med. Sci.*, 55, 801–805, 1993.
Srivastava et al., *Nature* 348, 747–749 (1990).
Vella et al., In: Robinson's Genetics for Cat Breeders and Veterinarians, Butterworth-Heinemann Medical, 4$^{th}$ edition. (1999).
Venkatachalam et al., *EMBO J.* 17, 4657–4667 (1998).
Verselis et al., *Oncogene* 19, 4230–4235 (2000).
Vinogradov, *Hereditas* 126, 95–102 (1997).
Yang et al., *Chromosome Res.*, 8, 393–404 (2000).

What is claimed is:

1. A method of detecting a susceptibility to a cancer in a cat comprising:

obtaining a biological sample chosen from either a normal tissue and a bodily fluid from the cat, wherein the biological sample from the cat includes at least one cell containing a germline DNA sequence for a p53 allele; and detecting a molecular biomarker in the biological sample obtained from the cat, wherein the molecular biomarker is a p53 allele comprising an insertion of a thymidine nucleotide at position 246, 247, or 248 of SEQ ID NO: 14 as compared to position 246, 247, or 248 of SEQ ID NO: 16, wherein the presence of the molecular biomarker is indicative of the cancer susceptibility in the cat.

2. The method of claim 1, wherein the detecting comprises contacting the sample with at least one nucleic acid segment, wherein the segment comprises SEQ ID NO: 1, 2, 3, 4, 5, 6, 7, 8, 9, 10, 11, 12 or 13.

3. The method of claim 1, wherein the cancer is sarcoma or a vaccine-associated feline sarcoma.

4. The method of claim 1, wherein the insertion of the thymidine nucleotide at position 246, 247 or 248 in SEQ ID NO: 14 as compared to position 246–247 as in SEQ ID NO: 16 is in an intron 7 of at least one of the alleles of a p53 gene nucleotide sequence.

5. A method of detecting a susceptibility to a vaccine-associated feline sarcoma (VAFS) in a cat comprising:

obtaining a biological sample chosen from either a normal tissue and a bodily fluid from the cat, wherein the biological sample from the cat includes at least one cell containing a germline DNA sequence for a p53 allele; and detecting a molecular biomarker in the biological sample obtained from the cat, wherein the molecular biomarker is a p53 allele comprising an insertion of a thymidine nucleotide at position 246, 247, or 248 of SEQ ID NO: 14 as compared to position 246, 247, or 248 of SEQ ID NO: 16, wherein the presence of the molecular biomarker is indicative of the VAFS susceptibility in the cat.

6. The method of claim 5, wherein the detecting comprises contacting the sample with at least one nucleic acid segment, wherein the segment comprises SEQ ID NO: 1, 2, 3, 4, 5, 6, 7, 8, 9, 10, 11, 12 or 13.

7. The method of claim 5, wherein the insertion of the thymidine nucleotide at position 246, 247 or 248 in SEQ ID NO: 14 as compared to position 246–247 as in SEQ ID NO: 16 is in an intron 7 of at least one of the alleles of a p53 gene nucleotide sequence.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Felis catus

<400> SEQUENCE: 1
tactcccctc ccctcaacaa                                              20
```

```
<210> SEQ ID NO 2
<211> LENGTH: 17
<212> TYPE: DNA
<213> ORGANISM: Felis catus

<400> SEQUENCE: 2
cagacctcgg gcggctc                                                  17

<210> SEQ ID NO 3
<211> LENGTH: 18
<212> TYPE: DNA
<213> ORGANISM: Felis catus

<400> SEQUENCE: 3
gtcggctctg actgtacc                                                 18

<210> SEQ ID NO 4
<211> LENGTH: 20
<212> TYPE: DNA
<213> ORGANISM: Felis catus

<400> SEQUENCE: 4
cttacctcgc ttagtgctcc                                               20

<210> SEQ ID NO 5
<211> LENGTH: 20
<212> TYPE: DNA
<213> ORGANISM: Felis catus

<400> SEQUENCE: 5
ctttgggacc ttctcttacc                                               20

<210> SEQ ID NO 6
<211> LENGTH: 20
<212> TYPE: DNA
<213> ORGANISM: Felis catus

<400> SEQUENCE: 6
attctccatc cagtggcttc                                               20

<210> SEQ ID NO 7
<211> LENGTH: 17
<212> TYPE: DNA
<213> ORGANISM: Felis catus

<400> SEQUENCE: 7
ccgccgttgg aactcac                                                  17

<210> SEQ ID NO 8
<211> LENGTH: 17
<212> TYPE: DNA
<213> ORGANISM: Felis catus

<400> SEQUENCE: 8
agtaaccgac ttggctg                                                  17

<210> SEQ ID NO 9
<211> LENGTH: 18
<212> TYPE: DNA
<213> ORGANISM: Felis catus

<400> SEQUENCE: 9
ggtttccatt tagggttc                                                 18
```

<210> SEQ ID NO 10
<211> LENGTH: 18
<212> TYPE: DNA
<213> ORGANISM: Felis catus

<400> SEQUENCE: 10
gcacggggca ggtcttcg                                                    18

<210> SEQ ID NO 11
<211> LENGTH: 20
<212> TYPE: DNA
<213> ORGANISM: Felis catus

<400> SEQUENCE: 11
ccagcatctc atccgagtgg                                                  20

<210> SEQ ID NO 12
<211> LENGTH: 20
<212> TYPE: DNA
<213> ORGANISM: Felis catus

<400> SEQUENCE: 12
ccctcactgc ctccagcttt                                                  20

<210> SEQ ID NO 13
<211> LENGTH: 20
<212> TYPE: DNA
<213> ORGANISM: Felis catus

<400> SEQUENCE: 13
ccctcactgc ctccagcttc                                                  20

<210> SEQ ID NO 14
<211> LENGTH: 268
<212> TYPE: DNA
<213> ORGANISM: Felis catus

<400> SEQUENCE: 14
gtagggaccc gcacgccacc ctgccccagg ccactctctc ccgtgctacc gcccatcccg      60
cctgtggaat cccgcctgt ggaatctcct ctgctgtccc ccacccctccg cctccaagtt    120 ttcttttctc tggctttggg accttctctt acccggcttc tcgatactcc ttaggctttt    180
aggctccaca taggatgaag gaggtgggga gtaaggggg ccccatctcc ctcactgcct     240
ccagctttct gtcttcttac gtgggtag                                        268

<210> SEQ ID NO 15
<211> LENGTH: 87
<212> TYPE: DNA
<213> ORGANISM: Felis catus
<220> FEATURE:
<221> NAME/KEY: misc_feature
<222> LOCATION: 15, 70
<223> OTHER INFORMATION: n = t or c
<220> FEATURE:
<221> NAME/KEY: misc_feature
<222> LOCATION: 20
<223> OTHER INFORMATION: n = g or a

<400> SEQUENCE: 15
gtaagcgggc aggangagan gaggcaggga gggtgcagtt cggctcaaaa tttactcttc      60
tctcgccgtn cctcacctct ttcccag                                          87

```
<210> SEQ ID NO 16
<211> LENGTH: 267
<212> TYPE: DNA
<213> ORGANISM: Felis catus
<220> FEATURE:
<221> NAME/KEY: misc_feature
<222> LOCATION: 14, 259
<223> OTHER INFORMATION: n = c or t.

<400> SEQUENCE: 16
gtagggaccc gcangccacc ctgccccagg ccactctctc ccgtgctacc gcccatcccg      60
cctgtggaat ccccgcctgt ggaatctcct ctgctgtccc ccaccctccg cctccaagtt     120
ttcttttctc tggctttggg accttctctt acccggcttc tcgatactcc ttaggctttt     180
aggctccaca taggatgaag gaggtgggga gtaagggggg ccccatctcc ctcactgcct     240
ccagcttctg tcttcttang tgggtag                                        267
```